US00PP21245P2

(12) United States Plant Patent
Kapiteijn

(10) Patent No.: US PP21,245 P2
(45) Date of Patent: Aug. 24, 2010

(54) ***ZANTEDESCHIA* PLANT NAMED 'CAPTAIN VENTURA'**

(50) Latin Name: *Zantedeschia sprengeri*
Varietal Denomination: Captain Ventura

(76) Inventor: Anthonius Simon Johannes Kapiteijn, Grasweg 38, Anna Paulowna, LJ (NL) 1761

( * ) Notice: Subject to any disclaimer, the term of this patent is extended or adjusted under 35 U.S.C. 154(b) by 0 days.

(21) Appl. No.: 12/380,503

(22) Filed: Feb. 27, 2009

(51) Int. Cl.
*A01H 5/00* (2006.01)

(52) U.S. Cl. ..... Plt./490

(58) Field of Classification Search ..... Plt./263, Plt./490
See application file for complete search history.

*Primary Examiner*—Susan B McCormick Ewoldt

(57) ABSTRACT

A new and distinct *Zantedeschia* cultivar named 'CAPTAIN VENTURA' is disclosed, characterized by large flowers, prolific flower production, strong peduncles, and green foliage occasionally spotted with white. The new variety is commercially suitable for indoor plant production.

1 Drawing Sheet

Figure 1:
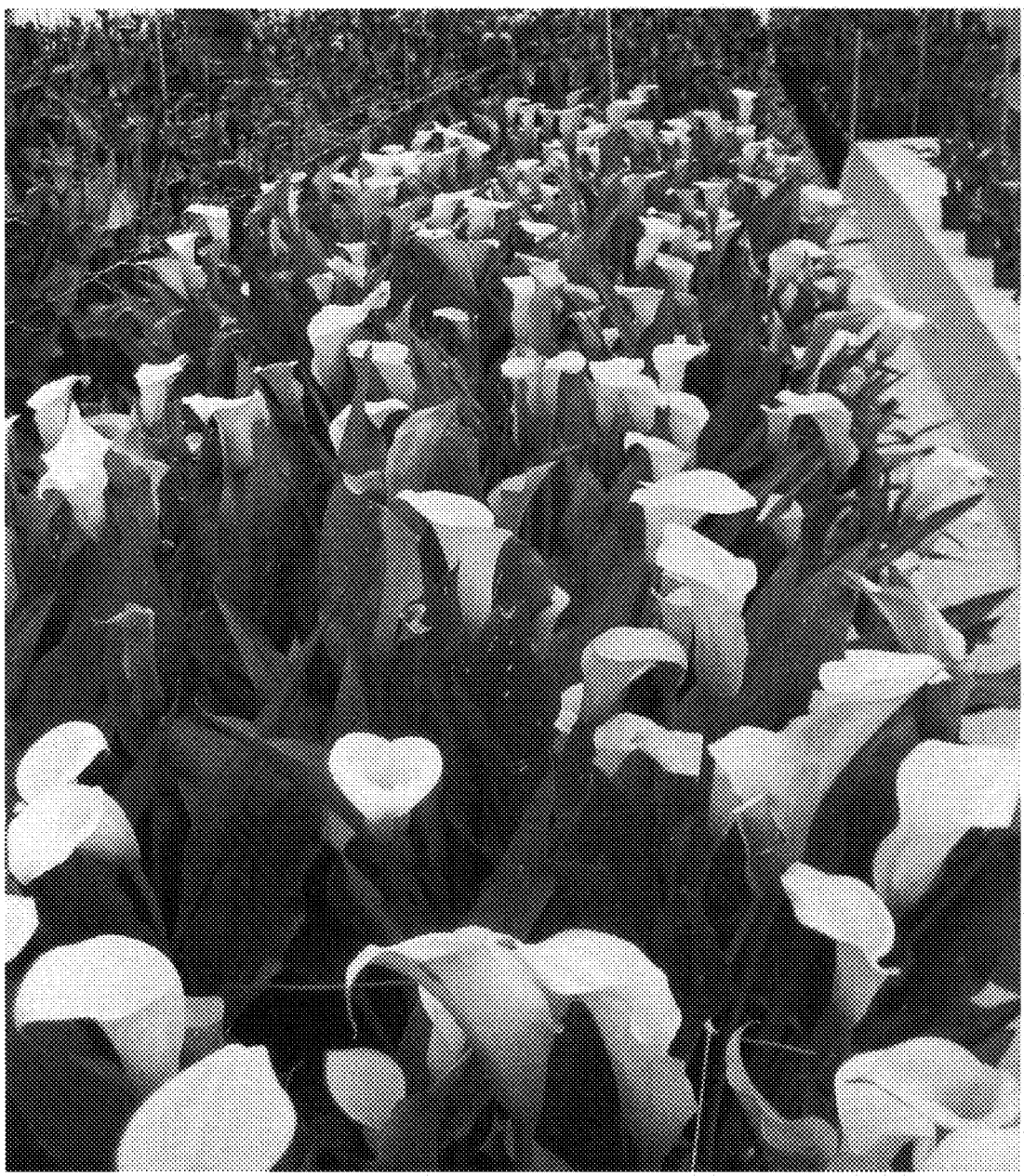

Latin name of the genus and species: *Zantedeschia sprengeri*.

Variety denomination: 'CAPTAIN VENTURA'.

BACKGROUND OF THE INVENTION

The new cultivar is a product of a planned breeding program. The new variety originated from a cross pollination, made by the inventor in 2002, of a proprietary seed parent identified as '44wit' and a proprietary pollen parent identified as '7849', both *Zantedeschia sprengeri*.

The new variety was discovered and selected by the inventor, Anthonius Simon Johannes Kapiteijn, a citizen of the Netherlands, in 2004 among a group of seedlings resulting from the crossing. The new cultivar was found in a commercial green house belonging to the inventor in Anna Paulowna, the Netherlands.

Asexual reproduction of the new cultivar 'CAPTAIN VENTURA' was first performed by micropropagation at a commercial laboratory in Ann Paulowna, the Netherlands in 2005. Micropropagated plants were subsequently grown out to produce tubers. 'CAPTAIN VENTURA' has been reproduced by both micropropagation and tubers and has shown that the unique features of this cultivar are stable and reproduced true to type.

SUMMARY OF THE INVENTION

The cultivar 'CAPTAIN VENTURA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CAPTAIN VENTURA.' These characteristics in combination distinguish 'CAPTAIN VENTURA' as a new and distinct *Zantedeschia* cultivar:

1. Large flowers.
2. Prolific flower production.

3. Strong peduncles.
4. Green foliage occasionally spotted with white.

PARENT COMPARISON

Plants of the new cultivar 'CAPTAIN VENTURA' are similar to plants of the seed parent variety, '44wit' in most horticultural characteristics, however, plants of the new cultivar produce larger flowers with longer stems.

Plants of the new cultivar 'CAPTAIN VENTURA' are similar to plants of the pollen parent variety, '7849' in most horticultural characteristics, however, plants of the new cultivar produce brighter white flowers.

COMMERCIAL COMPARISON

Plants of the new cultivar 'CAPTAIN VENTURA' are similar to plants of the unpatented variety, *Zantedeschia sprengeri* 'Crystal Blush' in most horticultural characteristics, however, plants of the new cultivar have larger, broader flowers. Additionally flowers of 'CAPTAIN VENTURA' do not turn pink with age as easily as 'Crystal Blush.'

BRIEF DESCRIPTION OF THE PHOTOGRAPH

The accompanying photograph in FIG. 1 illustrates in full color typical plants of 'CAPTAIN VENTURA' grown in a greenhouse in the Netherlands. The plants are approximately 2 years old, shown growing in ground beds. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'CAPTAIN VENTURA' plants grown in a climate controlled greenhouse in the Netherlands. Night temperature was around 17° C. and day temperatures were around 24° C. No artificial light, photoperiodic treatments or chemical treatments were given to the plants. Measurements and numerical values represent averages of typical plant types.

Botanical classification: *Zantedeschia sprengeri* cultivar 'CAPTAIN VENTURA.'

PROPAGATION

Time to initiate roots: Approximately 21 days from tissue culture plantlet at approximately 12 to 25° C.

Typical propagation material: Plants for commercial flowering potted plant production are typically produced by planting a 2 year old tuber.

Root description: Fine, fibrous.

PLANT

Growth habit: Leaves growing directly from base of plant, with no stems.

Plant shape: Upright, leaves slightly arching out, as inverted triangle.

Height: Approximately 48.8 cm from soil to top of highest leaf, approximately 77.1 cm to top of highest spathe.

Plant spread: Approximately 71.8 cm in a 6 inch pot.

Normal pot size: 6 inch and larger.

Growth rate: Moderate.

Branching characteristics: No branching, clump forming. Leaves emerge direct from base of plant.

Number of clumps per plant: 5.

Number of leaves per clump: Average 4.

Number of leaves per plant: Approximately 20.

Age of plant described: Approximately 6 months old, grown from a 2 year old tuber.

FOLIAGE

Leaf:

*Arrangement.*—Single leaves emerging basally.

*Average length(excluding petiole).*—Approximately 32.1 cm.

*Average width.*—Approximately 8.9 cm.

*Shape of blade.*—Narrow ovate.

*Aspect.*—Entire, undulate; lower half of each leaf more undulate than upper half.

*Apex.*—Aristate.

*Base.*—Attenuate.

*Margin.*—Entire.

*Texture of top surface.*—Glabrous, slightly leathery.

*Texture of bottom surface.*—Glabrous, slightly leathery.

*Color.*—Young foliage upper side: Near R.H.S. Green to yellow-green; in between 143A and 144A, occasionally with a few small dots, colored green-white; 157C. Young foliage under side: Near R.H.S. Yellow-green 144A, occasionally with a few small dots, colored green-white; 157C. Mature foliage upper side: Near R.H.S. Green to yellow-green; in between 137A and 146A, dotted white N155A and green-white; 157C, average length of dots: 9 mm, average width of dots 1.5 mm. Mature foliage under side: Near R.H.S. Green to yellow-green; in between 143A and 146A , dotted white; N155A, average length of dots: 9 mm, average width of dots 1.5 mm.

Venation:

*Type.*—Pinnate.

*Venation coloration upper side.*—Near RHS Yellow-Green 144A.

*Venation coloration under side.*—Near RHS Yellow-Green 144A.

Petiole:

*Length.*—Approximately 48 cm.

*Petiole diameter, distal.*—0.8 cm.

*Petiole diameter, proximal.*—1.1 cm.

*Color.*—Near RHS Yellow-green; 144B, base lighter; 145C.

*Strength.*—Very strong.

*General characteristics.*—Rounded with one undeep rib lengthways, smooth, slightly glossy.

Geniculum: Not present.

Wing:

*Length.*—Approximately 22.4 cm.

*Diameter.*—Approximately 0.3 cm.

*Color.*—Near RHS Yellow-green 145C.

INFLORESCENCE

Arrangement: Spathes with spadices held above the foliage on erect peduncles arising from the leaf axils of the clumps.

Flowering habit: Continuous.

Quantity of spathes per plant: On average 6 fully open spathes in good condition.

Natural flowering season: Autumn to early Spring.

Time to flowering: Approximately 6 months after planting a 2 year old tuber.

Fragrance: Not present.

Self-cleaning or persistent: Persistent

Flower longevity: Flowers stay in good condition approximately 30 days on the plant.

Spathe:

*Aspect.*—Strongly cupped with wavy margin.

*Length.*—Approximately 9.0 cm.

*Width.*—Approximately 6.2 cm.

*Depth.*—Approximately 7.4 cm.

*Shape.*—Broad ovate.

*Margin.*—Entire, wavy.

*Apex.*—Mucronate.

*Base.*—Cuneate.

*Color.*—Front when opening: Near RHS Green-white; 157C, more yellow-green towards the top; 150D, outer tip green; 143A. Back when opening: Near RHS Yellow-green to green-white; in between 150D and 157C but lighter, more yellow-green towards the top; 150D, base yellow-green; 144B, outer tip green; 143A. Front when mature: Near RHS White to green-white; in between 155C and 157D, outer tip green; 143A. Back when mature: Near RHS Green-white; 157D, base yellow-green; 145A, outer tip green; 143A. Fading to: Not fading.

Spadix:

*Shape.*—Columnar, arising from the top of the peduncle.

*Tip.*—Obtuse.

*Base.*—Obtuse.

*Length.*—Approximately 2.7 cm.

*Diameter.*—Approximately 0.6 cm.

*Color.*—Immature: Lower part (female flowers) Near RHS yellow-green 150C. Upper part (male flowers) Near RHS yellow 11A. Mature: Lower part (female parts) Near RHS yellow-green 145A. Upper part (male parts) Near RHS yellow 13B.

*Quantity of flowers per spadix.*—Approximately 30 female, 200 male.

*Spadix flower arrangement.*—Flowers unisexual, female parts rounded in cross-section, single; male parts irregularly oblong.

*Spadix flower diameter.*—Female parts average: 3.5 mm. Male parts average: 1 mm.

*Spadix flower depth.*—Female parts average: 2 mm. Male parts average: less than 0.5 mm.

Peduncle:

*Length.*—Approximately 69.4 cm.

*Diameter.*—Approximately 0.8 cm.

*Color.*—Near RHS Yellow-green 144B, darker towards the top, near 144A, lighter towards the base, near 145D.

*Strength.*—Moderate.

*Angle.*—Average angle: 10° (straight upright=0°).

REPRODUCTIVE ORGANS

*Anther color.*—Near RHS Yellow-orange 13B.

*Pollen color.*—Near RHS Yellow 4D.

*Quantity pollen.*—Moderate to profuse.

*Stigma color.*—Near RHS Yellow 13A.

*Ovary color.*—Near RHS Yellow-green 145A.

OTHER CHARACTERISTICS

Disease resistance: Neither resistance nor susceptibility to diseases or pests has been observed in this variety.

Drought tolerance and temperature tolerance: The new cultivar is a typical *Zantedeschia,* tolerant of temperatures approximately 9° to 30° C. and does not tolerate drought.

Fruit/seed production: Not observed.

What is claimed is:

1. A new and distinct cultivar of *Zantedeschia* plant named 'CAPTAIN VENTURA' as herein illustrated and described.

* * * * *